United States Patent [19]
Bark et al.

[11] Patent Number: 5,354,283
[45] Date of Patent: Oct. 11, 1994

[54] TROCAR RETENTION APPARATUS

[75] Inventors: Jeffrey E. Bark, Green Bay; Andrea Potokar; Patrick G. Lennon, both of De Pere, all of Wis.

[73] Assignee: Little Rapids Corporation, Green Bay, Wis.

[21] Appl. No.: 179,017

[22] Filed: Jan. 7, 1994

[51] Int. Cl.$^5$ ............................................. A61M 25/02
[52] U.S. Cl. ......................... 604/180; 128/DIG. 26
[58] Field of Search .................. 604/174, 180, 177; 128/DIG. 26

[56] References Cited

U.S. PATENT DOCUMENTS

| | | | |
|---|---|---|---|
| 2,008,340 | 7/1935 | Salvati et al. | 128/215 |
| 2,402,306 | 6/1946 | Turkel | 128/215 |
| 2,590,006 | 3/1952 | Gordon | 604/180 |
| 3,017,887 | 1/1962 | Heyer | 128/DIG. 26 |
| 3,288,137 | 11/1966 | Lund | 128/133 |
| 3,487,837 | 1/1970 | Petersen | 604/180 |
| 3,782,388 | 1/1974 | Page | 604/180 |
| 3,817,251 | 6/1974 | Hasson | 128/348 |
| 3,900,026 | 8/1975 | Wagner | 128/133 |
| 4,055,385 | 10/1977 | Bjors | 85/1 |
| 4,077,412 | 3/1978 | Moossun | 128/347 |
| 4,230,110 | 10/1980 | Beroff | 128/214.4 |
| 4,287,891 | 8/1981 | Peters | 128/34 |
| 4,318,401 | 3/1982 | Zimmerman | 128/214 |
| 4,392,853 | 7/1983 | Muto | 604/171 |
| 4,392,854 | 7/1983 | Ibach | 604/174 |
| 4,419,094 | 12/1983 | Patel | 604/93 |
| 4,435,174 | 3/1984 | Redmond et al. | 604/174 |
| 4,435,175 | 3/1984 | Friden | 604/177 |
| 4,519,793 | 5/1985 | Galindo | 604/180 |
| 4,533,349 | 8/1985 | Bark | 604/174 |
| 4,555,243 | 11/1985 | Markham | 604/263 |
| 4,574,798 | 3/1986 | Heitzman | 128/205.22 |
| 4,579,120 | 4/1986 | MacGregor | 128/640 |
| 4,583,977 | 4/1986 | Shishov et al. | 604/174 |
| 4,585,443 | 4/1986 | Kaufman | 604/174 |
| 4,593,681 | 6/1986 | Soni | 128/4 |
| 4,642,101 | 2/1987 | Krolikowkski et al. | 604/164 |
| 4,645,492 | 2/1987 | Weeks | 604/180 |
| 4,650,473 | 3/1987 | Bartholomew et al. | 604/174 |
| 4,658,813 | 4/1987 | Jones | 128/207.14 |
| 4,675,006 | 6/1987 | Hrushesky | 604/180 |
| 4,686,977 | 8/1987 | Cosma | 128/DIG. 26 |
| 4,737,143 | 4/1988 | Russell | 604/180 |
| 4,743,231 | 5/1988 | Kay et al. | 604/180 |
| 4,755,173 | 7/1988 | Konopka et al. | 604/167 |
| 4,767,411 | 8/1988 | Edmunds | 604/180 |
| 4,772,268 | 9/1988 | Bates | 604/174 |
| 4,792,330 | 12/1988 | Lazarus et al. | 604/174 |
| 4,798,595 | 1/1989 | Andersson et al. | 604/174 |
| 4,808,162 | 2/1989 | Oliver | 604/180 |
| 4,834,712 | 5/1989 | Quinn et al. | 604/175 |
| 4,883,053 | 11/1989 | Simon | 128/303 |
| 4,897,081 | 1/1990 | Poirier et al. | 604/175 |
| 4,906,233 | 3/1990 | Moriuchi et al. | 604/174 |
| 4,931,056 | 6/1990 | Ghajar et al. | 606/130 |
| 4,966,589 | 10/1990 | Kaufman | 604/174 |
| 4,976,698 | 12/1990 | Stokley | 604/174 |
| 4,981,475 | 1/1991 | Haindi | 604/174 |
| 5,002,557 | 3/1991 | Hasson | 606/191 |
| 5,073,166 | 12/1991 | Parks et al. | 609/93 |
| 5,073,169 | 12/1991 | Raiken | 604/180 |
| 5,074,847 | 12/1991 | Greenwell et al. | 604/174 |
| 5,078,689 | 1/1992 | Keller | 604/167 |
| 5,188,609 | 2/1993 | Bayless et al. | 604/180 |
| 5,215,531 | 6/1993 | Maxson et al. | 604/180 |
| 5,305,742 | 4/1994 | Styers et al. | 128/DIG. 26 |

Primary Examiner—Paul J. Hirsch
Attorney, Agent, or Firm—Niro, Scavone, Haller & Niro

[57] ABSTRACT

An apparatus for stabilizing a trocar inserted through the skin of a patient during a medical procedure that provides the operating personnel with the ability to adjust the angle of orientation of the inserted trocar with respect to the patient and rotate the trocar as desired after insertion into the patient. The apparatus is attached to the skin of the patient and the trocar movement is facilitated by a trocar receivable rotatable spheroid frictionally retained in a stabilizing member. The apparatus provides for a secure, yet, adjustable surgical aid.

31 Claims, 1 Drawing Sheet

TROCAR RETENTION APPARATUS

FIELD OF THE INVENTION

Currently, a surgical technique known as "minimally invasive surgery" is growing in popularity. Such minimally invasive surgical techniques include arthroscopic surgery on a joint, such as the knee, or other types of surgery, such a laporoscopic cholecystectomy or laporoscopic lymphadenectomy. The advantages of the minimally invasive surgical technique include reduced blood loss, minimal scarring, minimized infection, shorter hospital stay and enhanced use on an outpatient basis.

Minimally invasive surgical techniques often require the use of trocars, cannulas or catheters which are inserted into the area of the patient upon which the surgical procedure is to be performed. The trocar can be used for insufflation of the surgical site, endoscopic viewing of the site, suction of the site, and incising, cauterizing and suturing the tissue involved. The trocars or cannulas are intended to remain relatively stable throughout the minimally invasive surgical procedure. However, rotation of the trocar may be advantageous, and sometimes may become necessary during the medical procedure. Rotation of the trocar, while inserted into a patient permits the operating personnel an enhanced view of the anatomy and provides better manipulation of the surgical instruments used in the procedure.

The present invention relates to a secure, yet, adjustable trocar retention apparatus that is attached to the skin of a patient upon whom a minimally invasive surgery is to be performed. The retention apparatus is specifically designed to stabilize the trocar or cannula during the surgical procedure while providing the operating personnel with the ability to adjust the angle of orientation of the inserted trocar with respect to the skin as well as the ability to rotate the trocar as desired after implantation into the patient. In the present invention the trocar can be inserted through the trocar retention apparatus after it has been secured to a patient. Alternatively, the trocar retention apparatus can be placed over a trocar that has been inserted into a patient. Currently, there is no apparatus available which perform these functions.

DESCRIPTION OF THE PRIOR ART

Some current approaches to control the entry angle of a trocar does not provide the flexibility to rotate and change the angle of inclination of the trocar prior to, or during, the insertion of trocar into the patient. The following U.S. Pat. Nos. describe variants on that approach: 4,966,589 (Kaufman); 2,402,306 (Turkel); 3,288,137 (Lund); 2,008,340 (Saluati, et al); and 4,585,443 (Kaufman). None of disclosed apparatus allows continuous, easy variation of the angle of inclination of the trocar after installation of the retaining apparatus. Nor do they provide the ability to place the apparatus about the trocar after insertion of the needle into the patient.

U.S. Pat. No. 4,675,006 (Hrushesky) discloses a retainer which is said to be able to accommodate some limited range of angles between a needle and patient's body. But, the Hrushesky reference does not disclose a ball and socket arrangement to provide both an adjustable angle with respect to the skin and the ability to rotate a trocar as desired after insertion into the patient, through the retaining apparatus. Moreover, the Hrushesky reference relates only to small diameter needles.

U.S. Pat. No. 4,479,120 (MacGregor) discloses a retention apparatus limited to maintaining a fixed 90° angle between the catheter and the skin of the patient. U.S. Pat. No. 4,519,793 (Galindo) describes another fixed angle apparatus.

SUMMARY OF THE INVENTION

The present invention is directed to a skin mounted trocar retention apparatus designed to stabilize the percutaneous trocar during a minimally invasive surgical procedure. The present invention is intended to provide a stable, yet, adjustable base for a trocar inserted through the skin of a patient. The present invention provides for the placement of the retention apparatus about the trocar after the trocar has been inserted into the patient.

Accordingly, one object of the present invention is to provide a trocar retention apparatus that stabilizes the trocar during a surgical procedure.

It is another object of the present invention to provide an adjustable trocar receptacle that maintains the angle of rotation and the angle of inclination of the trocar after the trocar has been inserted in the retention apparatus.

It is another object of the present invention to provide a means to secure the trocar retention apparatus to the patient.

It is another object of the invention to secure the trocar at a setting preferred by the operating personnel after installation of the trocar into the retention apparatus.

It is a further object of the present invention to provide for the installation of the trocar retention apparatus after the trocar has been inserted in the patient.

It is yet another object of the present invention to provide passageways in the retention apparatus allowing fluids secreted from the patient to drain away from the point of trocar insertion.

It is still another object of the present invention to allow for the continuous, easy variation of the angle of insertion of the trocar, either before or after installation of the trocar through the retaining apparatus.

DETAILED DESCRIPTION OF THE PREFERRED EMBODIMENT

Figure 1:
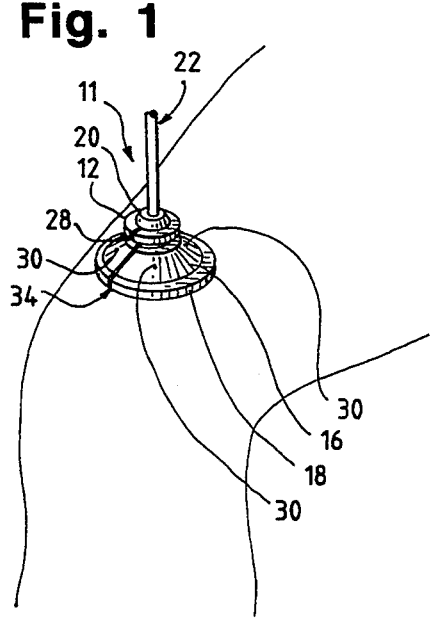
FIG. 1 shows a perspective view of the invention of surgical procedures, positioned for an operation on the knee of a patient.

FIG. 1 illustrates the trocar retention apparatus in a position for a minimally intrusive surgical procedure preformed on the knee of a patient. The trocar retention apparatus is the term used to describe the entire mechanism.

FIGS. 1–4 generally show the frusto-conical shaped trocar retention apparatus.

The trocar retention device 11 has a rotatable spheroid 20 that is supported by a stabilizing member 10. The stabilizing member has a top disc 12, a base disc 18 and an exterior wall 16. The top disc 12 of the stabilizing member 10 contains a socket 14 in which a rotatable spheroid 20 is frictionally retained. The rotatable spheroid 20 has a cylindrical bore 24 that is adapted to slidably receive a trocar 22. The trocar retention apparatus possesses a slit 34 to enable the retention apparatus to be fitted over a trocar 22 after it has been inserted in a patient. The stabilizing member 10 also possesses a tie groove 28 between the exterior wall 16 and the top disc 12 that aids in holding the stabilizing member 10 in place about the trocar 22. Further, a plurality of suture holes 30 are disposed around exterior wall 16 of the stabilizing member 10.

Figure 4:
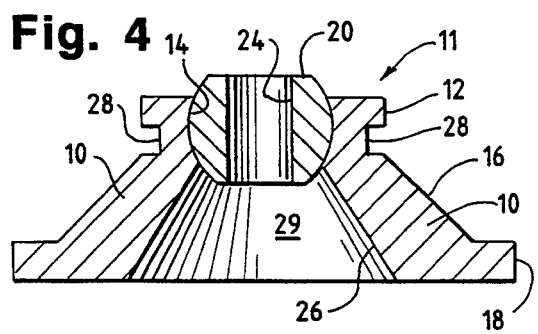
FIG. 4 shows a sectional view of the present invention.

FIG. 4 is a sectional view that illustrates the interior wall 26 of the stabilizing member 10 that is contiguous to the exterior wall 16 of the stabilizing member 10, with the interior wall 26 forming a trocar receptacle chamber 29.

The base disc 18, the top disc 12, the exterior wall 16, the interior wall 26 and the tie groove 28 all form the stabilizing member 10 and can be constructed of one unitary structure molded from a material such as silicone elastomer, rubber, plastic or the like. The material selected should provide comfort to the patient while at the same time providing stability to the trocar 22. Although, the preferred shape of the stabilizing member 10 is frusto-conical, it may be any three dimensional shape so long as the socket 14 and preferably the tie groove 28 are present.

The trocar 22 can be inserted into the trocar retention apparatus in one of two ways. The first method is to place the base disc 18 of the stabilizing member 10 against the skin of the patient near the location the surgery is to be performed. The trocar 22 is then inserted through the cylindrical bore or aperture 24 in the rotatable spheroid 20, through the trocar receptacle chamber 29 and then the trocar 22 is inserted through the skin of the patient.

A second method utilized in the placement of the trocar retention apparatus (illustrated in FIGS. 2 and 3) is somewhat different. Utilizing the second method of insertion, the trocar 22 is inserted into the patient prior to the placement of the trocar retention apparatus. In utilizing the second method of placement, the trocar retention apparatus must incorporate a slit 34 that extends from the base disc 18 to the top disc 12 of the stabilizing member 10 and protrudes from the exterior wall 16 through the interior wall 26 of the stabilizing member 10. The slit 34 also protrudes through the rotatable spheroid 20 to the cylindrical bore or aperture 24. The slit 34 is adapted to enable the trocar retention apparatus to be fitted over the trocar 22 after it has been inserted in a patient. After the trocar 22 is inserted in the patient, the stabilizing member 10 and the rotatable spheroid 20 are manipulated to cause the slit 34 to open such that the trocar retention apparatus can be placed about the trocar 22, such that the trocar 22 is nestled in the opening 24 of the rotatable spheroid 20. The trocar retention apparatus can then be positioned about the patient. The spheroid securing groove or tie groove 28 may be secured by a tie, clamp or suture, once the trocar 22 is in place to hold the slit 34 along the stabilizing member 10 in a closed position. The slit 34 in the stabilizing member 10 and rotatable spheroid 20 to is an alternative embodiment that may be used in practice of the present invention.

FIG. 4 illustrates the trocar receptacle chamber 29 and the rotatable spheroid 20. The rotatable spheroid 20 is frictionally retained within the socket 14 located along the top disc 12 of the stabilizing member 10. The rotatable disc 20 has a cylindrical bore or aperture 24 to receive the trocar 22. The rotatable spheroid 20 compliments the socket 14. The rotatable spheroid 20 and socket 14 may have a smooth, toothed or roughened surface in order to provide various levels of adjustability.

The rotatable spheroid 20 may be constructed of the same material as the stabilizing member 10 or it may be made of other material such as polyethylene or stainless steel. The rotatable spheroid 20 is rotatable over a 360° angle of rotation to provide the operating personnel a better view of the surgical area or provide easier and more stable manipulation of the surgical instruments. Rotation of a trocar 22 may be desirable, for example, to clear an occlusion of one of the catheter openings within a blood vessel or other organ, as may become necessary from time to time during hemodialysis or to maneuver the apparatus around tendons and cartilage during arthroscopic surgery.

The interior walls 26 of the stabilizing member 10 also aids in the surgical procedure by limiting the inclination angle of the trocar 22 when it is inserted through the aperture 24 of the rotatable spheroid 20. The interior walls 26 of the stabilizing member 10 are inclined, preferably at a 45° angle to the skin of the patient, to prevent the trocar 22 from becoming dislodged during the surgical procedure. In essence, the interior walls 26 of the stabilizing member 10 limit the angle of inclination of the trocar 22.

The stabilizing member 10 also has a tie groove 28 which is adapted to receive a clamp, tie, suture or other similar fastening apparatus. The tie groove 28 is located between the exterior wall 16 and the top disc 12 of the stabilizing member. The tie groove 28 operates to secure the rotating spheroid 20 in place once the desired angle or rotation and declination of the trocar 22 has been obtained. After installation of the trocar 22, the rotatable spheroid 20 is secured in place, by tightening a clamp or suture around the tie groove 28. The tightening of the suture places a compressive force on the tie groove 28 which in turn places a compressive force on the rotatable spheroid 20. The angle of rotation and inclination of the trocar 22 can be changed, and the trocar 22 can be rotated as desired by the operating personnel simply by loosening the clamp or suture that assists in holding the rotatable spheroid 20 in a fixed position. The newly chosen position of the trocar 22 can then be secured once again, by tightening the clamp or suture located in the groove 28.

Figure 2:
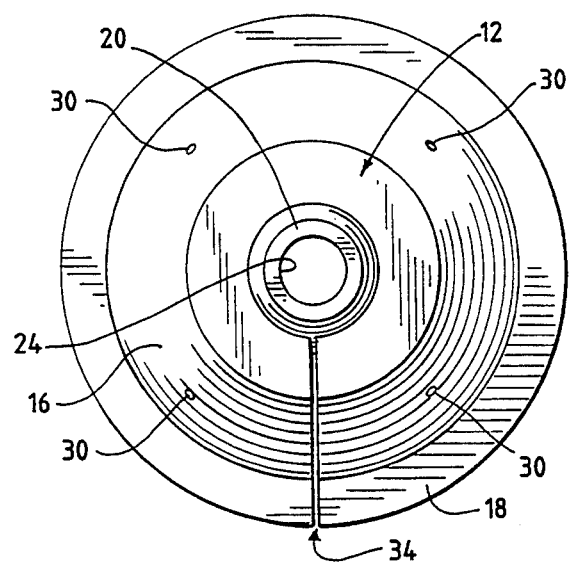
FIG. 2 shows a plan view of the present invention.
Figure 3:
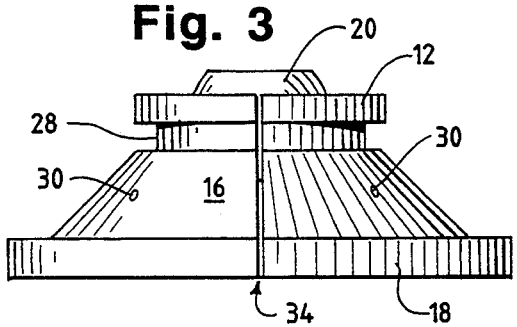
FIG. 3 shows a side view of the present invention.

FIGS. 1–3 demonstrate a plurality of suture holes 30 which may be disposed about the periphery of the exterior wall 16 of the stabilizing member 10. The suture holes 30 extend from the exterior wall 16 through the bottom of the base disc 18. The purpose of the suture holes 30 is to permit the stabilizing member 10 to be anchored to the patents skin by extending a suture through the suture hole 30, through the patients skin, and through the adjacent suture hole 30 to secure the stabilizing member 10 to the patient.

Figure 5:
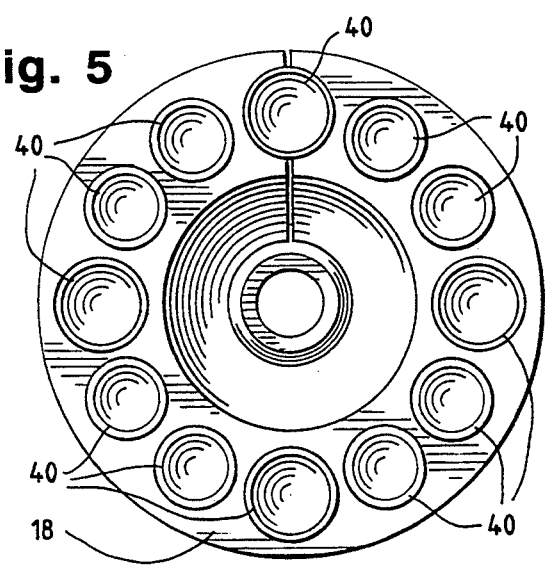
FIG. 5 shows a plan view of an embodiment of the present invention having suction cups secured to the base.

FIG. 5 illustrates an alternative method of securing the trocar retention apparatus to the patient by means of a plurality of suction cups 40 positioned about the bottom of the base disc 18 of the trocar retaining apparatus. The suction cups 40 secure the stabilizing member 10 to the patient. The suction cups 40 provide for short term attachment of the stabilizing member 10 during surgery, rather than long term therapy. Alternatively, double sided medical tape or a contact medical adhesive may be used to secure the stabilizing member 10 to the skin of the patient.

Figure 6:
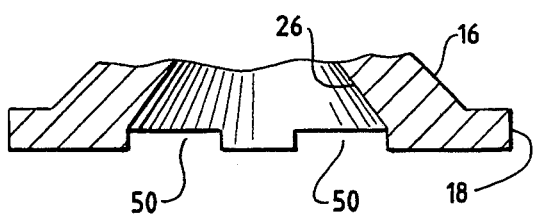
FIG. 6 shows a sectional view of the embodiment of FIG. 1 containing drainage grooves.

FIG. 6 illustrates an alternative embodiment that incorporates a plurality of drainage canals 50 within the base disc 18 of the stabilizing member 10. The drainage canals 50 extend from the base of the interior wall 26 to the base disc 18 of the stabilizing member 10. The drainage canals 50 allow fluids secreted from the patient to drain away from the point the trocar is inserted in the patient. The drainage canals 50 can be used in connection with any of the above referenced embodiments.

It will be appreciated by those skilled in the art that various changes and modifications can be made to the illustrated embodiments without departing from the spirit of the present invention. All such modifications and changes are intended to be covered by the following claims.

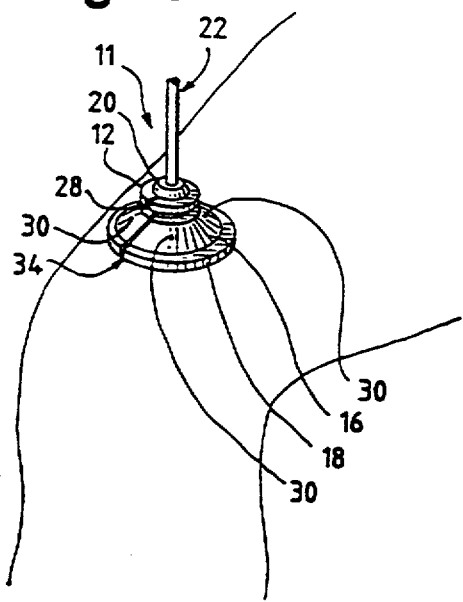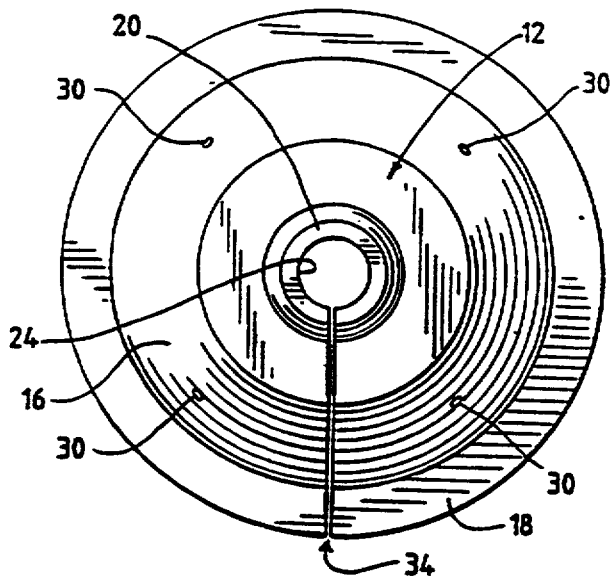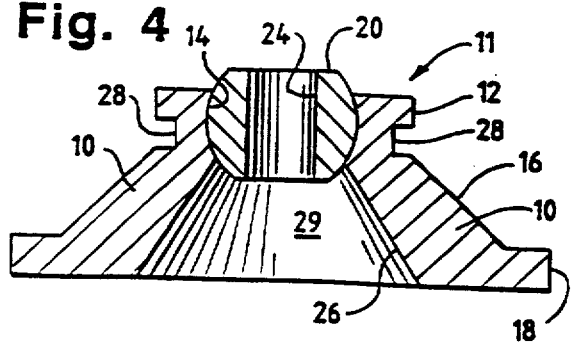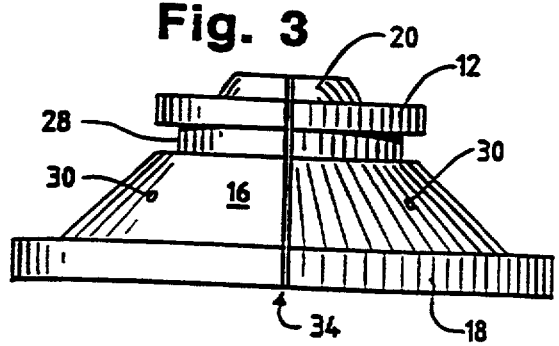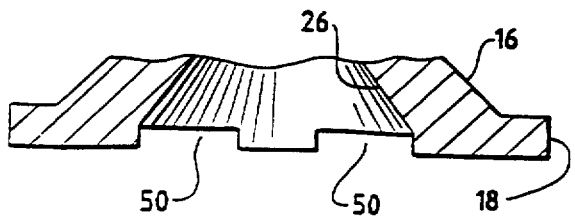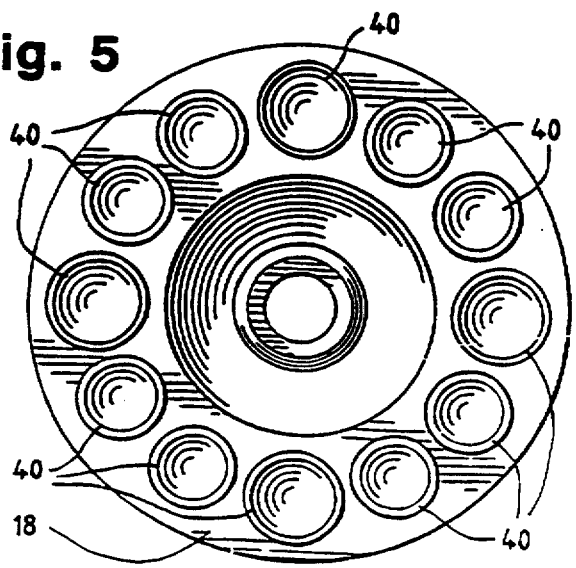

We claim:

1. A trocar retention apparatus for stable but adjustable positioning of a trocar inserted through the skin of a patient comprising:
    a stabilizing member having a base, an exterior wall and a top;
    a rotatable spheroid rotatably affixed to said top of said stabilizing member having an aperture adapted to slidably receive a trocar inserted through said aperture;
    an interior wall forming a trocar receptacle chamber to slidably receive said trocar inserted through said aperture; and
    means for securing said stabilizing member to the patient.

2. The trocar retention apparatus of claim 1, wherein said stabilizing member has a generally frusto-conical shape.

3. The trocar retention apparatus of claim 1, wherein said stabilizing member has a domed shape.

4. The trocar retention apparatus of claim 1, wherein said stabilizing member has a pyramidal shape.

5. The trocar retention apparatus of claim 1, further comprising a socket within said stabilizing member to frictionally retain said rotatable spheroid.

6. The trocar retention apparatus of claim 5, wherein said interior side walls limit the angle of inclination of the trocar with respect to the skin of the patient.

7. The trocar retention apparatus of claim 6, wherein the angle of inclination is limited to 45°.

8. The trocar retention apparatus of claim 7, wherein the angle of inclination is limited to 60°.

9. The trocar retention apparatus of claim 6, wherein said interior sidewalls form a frusto-conical shaped trocar receptacle chamber.

10. The trocar retention apparatus of claim 9, wherein said rotating spheroid has a flat side to receive the trocar.

11. The trocar retention apparatus of claim 1, wherein said means for securing comprise a plurality of suction cups affixed to the base of said stabilization member.

12. The trocar retention apparatus of claim 1, wherein said means for securing comprise a plurality of suture holes disposed about said exterior sidewall adapted to receive suture material.

13. The trocar retention apparatus of claim 1, wherein said means for securing comprise double sided adhesive tape affixed to said base of said stabilization member.

14. The trocar retention apparatus of claim 1 further comprising a tie groove within said exterior wall adapted to receive a securing apparatus to secure said rotatable spheroid in the position desired by the operating personnel.

15. The trocar retention apparatus of claim 14, wherein said securing apparatus comprises a clamp.

16. A trocar retention apparatus for stable but adjustable positioning of a trocar inserted through the skin of a patient comprising:
    a stabilizing member having a base, an exterior wall and a top;
    a socket formed in said top of said stabilizing member;
    a rotating spheroid frictionally retained in said socket having an aperture adapted to slidably receive a trocar inserted through said aperture;
    a slit extending through said stabilization member and rotating spheroid adapted to insertably receive said trocar;
    a means for securing said stabilization member to the patient.

17. The trocar retention apparatus of claim 16, wherein said stabilizing member has a generally frusto-conical shape.

18. The trocar retention apparatus of claim 16, wherein said stabilizing member has a domed shape.

19. The trocar retention apparatus of claim 16, wherein said means for securing comprise a plurality of suction cups affixed to the base of said stabilization member.

20. The trocar retention apparatus of claim 16, wherein said means for securing comprise a plurality of suture holes disposed about said exterior sidewall adapted to receive suture material.

21. The trocar retention apparatus of claim 16, wherein said means for securing comprise double sided adhesive tape affixed to said base of said stabilization member.

22. The trocar retention apparatus of claim 16, further comprising a tie groove positioned along said exterior wall.

23. The trocar retention apparatus of claim 22, further comprising a securing apparatus adapted to cooperate with said tie groove to secure said trocar and rotatable spheroid in the position desired by the operating personnel.

24. The trocar retention apparatus of claim 23, wherein said securing apparatus comprises a clamp.

25. The trocar retention apparatus of claim 24, wherein said securing apparatus comprises a suture.

26. A trocar retention apparatus for stable but adjustable positioning of a trocar inserted through the skin of a patient, comprising:
    a stabilizing member having a base, an exterior wall and a top;
    a socket formed in said top of said stabilizing member;
    a rotatable spheroid frictionally retained in said socket having an aperture adapted to slidably receive a trocar inserted through said aperture;
    a drainage passageway integral to said retention apparatus;
    a means for securing said stabilization member to the patient.

27. The trocar retention apparatus of claim 26, wherein said drainage passageway is integral to said base of said stabilization member.

28. The trocar retention apparatus of claim 26, wherein said means for securing comprise a plurality of suction cups affixed to the base of said stabilization member.

29. A trocar retention apparatus of claim 28, further comprising a tie groove, within said exterior wall, adapted to receive a securing apparatus to secure said rotatable spheroid in the position desired by the operating personnel.

30. The trocar retention apparatus of claim 26, wherein said means for securing comprises a plurality of suture holes disposed about said exterior sidewall adapted to receive suture material.

31. The trocar retention apparatus of claim 30 further comprising a tie groove, within said exterior wall, adapted to receive a securing apparatus to secure said rotatable spheroid in the position desired by the operating personnel.

* * * * *

UNITED STATES PATENT AND TRADEMARK OFFICE
CERTIFICATE OF CORRECTION

PATENT NO. : 5,354,283  
DATED : October 11, 1994  
INVENTOR(S) : Jeffrey E. Bark, Andrea Potokar, and Patrick Lennon Page 1 of 2

It is certified that error appears in the above-indentified patent and that said Letters Patent is hereby corrected as shown below:

In the Drawing, delete the drawings consisted of figures 1-6, and substitute therefor the drawings, consisted of figures 1-6, as shown on the attached page.

Signed and Sealed this

Tenth Day of January, 1995

Attest:

BRUCE LEHMAN

Attesting Officer

Commissioner of Patents and Trademarks